United States Patent [19]
Narciso, Jr.

[11] Patent Number: 5,441,497
[45] Date of Patent: Aug. 15, 1995

[54] LIGHT DIFFUSING GUIDEWIRE

[75] Inventor: Hugh L. Narciso, Jr., Santa Barbara, Calif.

[73] Assignee: PDT Cardiovascular, Inc., Santa Barbara, Calif.

[21] Appl. No.: 275,029

[22] Filed: Jul. 14, 1994

[51] Int. Cl.$^6$ ............................................ A61B 17/36
[52] U.S. Cl. ........................................ 606/15; 606/7; 606/16
[58] Field of Search .............................. 606/7, 14–17; 128/772

[56] References Cited

U.S. PATENT DOCUMENTS

| | | | |
|---|---|---|---|
| 4,860,743 | 8/1989 | Abela | 606/15 |
| 5,019,075 | 5/1991 | Spears et al. | 606/7 |
| 5,095,911 | 3/1992 | Pomeranz | 128/772 X |
| 5,109,830 | 5/1992 | Cho | 606/7 X |
| 5,151,096 | 9/1992 | Khoury | 606/17 X |
| 5,188,634 | 2/1993 | Hussein et al. | 606/7 X |
| 5,196,005 | 3/1993 | Doiron et al. | 606/7 |

Primary Examiner—Peter A. Aschenbrenner
Attorney, Agent, or Firm—Michael G. Petit

[57] ABSTRACT

A light diffusing guidewire which has the ability to deliver light to luminal surfaces such as blood vessels for the diagnosis and treatment of medical conditions. The device can be used either in conjunction with another outer catheter such as a balloon catheter or as a stand-alone device. The light diffusing guidewire can be used as a standard guidewire for directing the placement of another catheter. The guidewire has an elongate body portion having a proximal end and a distal (invasive) end. A portion of the body portion transmits light from the proximal end to a light diffusing element within the body portion near the distal end. The guidewire has a floppy tip distal to the light diffusing element and is rigid and highly torqueable proximal to the diffusing element. The outer diameter of the guidewire is similar to that of standard interventional guidewires such as angioplasty guidewires, i.e. 0.014"–0.038". The light diffusing guidewire has a low profile which enables delivery of illuminating diagnostic or treatment light to the walls of even the most distal, small-diameter vessels.

11 Claims, 2 Drawing Sheets ial aspects of the invention in a familiar context and
LIGHT DIFFUSING GUIDEWIRE

BACKGROUND OF THE INVENTION

1. Field of the Invention

This invention relates to a device for illuminating the walls of a tubular tissue within the body of a mammal and more particularly to a flexible, steerable illuminating guidewire which may be used to deliver light to the walls of a tubular tissue.

2. Prior Art

It is helpful when discussing the prior art relating to the present invention to illustrate state of the art light delivery in the context of a particular medical application such as Photodynamic Therapy (PDT). PDT has been shown to be a very effective method for treating tumors. PDT has also been proposed for the treatment of cardiovascular disease. Light interaction with tissue with or without exogenous chromophores being present has also been proposed as a diagnostic tool employing fluorescence, Raman scattering, and/or Raleigh scattering measurements. Delivery of light from a source such as a laser to the treatment sight is accomplished through the use of a single-fiber delivery system with special light diffusing tips affixed thereto. As the field of PDT matures, new light delivery systems are needed to treat specific sites. One particular need arises due to the inability of prior art light delivery systems to treat the wall of tubular tissue having very small diameter lumen. Extremely flexible prior art light diffusing catheters are normally inserted over a guidewire and, therefore, have a relatively large profile. Others lacking a guidewire lumen, are low profile and relatively rigid and unsteerable.

Examples of light delivery systems for illuminating the walls of vessels within the body include a single fiber, cylindrical diffuser (U.S. Pat. No. 5,196,005); a spherical diffuser (U.S. Pat. No. 4,693,556); a microlensing system (U.S. Pat. No. 5,231,684); and an over-the-wire cylindrical diffusing, multi-fiber-optic catheter (U.S. Pat. No. 5,169,395). An example of a light transmitting diagnostic catheter is disclosed in U.S. Pat. No. 5,217,456 entitled: Intravascular Optical Radial Imaging System by the present inventor. While these catheters have their particular uses in delivering diffuse light to the walls of some tubular tissues of the body, they are not generally suitable for delivery to the walls of very small diameter tubular tissues.

A light diffusing catheter for use in the vasculature of the body is described by Narciso, Jr. in U.S. Pat. No. 5,169,395. This light diffusing catheter delivers therapeutic levels of light to a treatment site located on the wall of a tubular tissue within the body. The catheter is introduced into the body percutaneously and directed to the particular treatment site via a guidewire. The guidewire acts to direct the light diffusing catheter. With a dedicated guidewire integral and coextensive with the body portion of the catheter, the catheter of the present invention need not have the high profile required by a catheter that fits over a guidewire.

A more low profile catheter for delivery of light is described by Doiron, et. al. in U.S. Pat. No. 5,196,005. The catheter described in the '005 patent is relatively low in profile and could be used for delivering light to the luminal wall of small blood vessels but the delivery of light to a particular treatment site is made difficult because of the lack of a steering capability. It is contemplated within the '005 patent that the catheter be delivered to the particular treatment site by means of a standard catheter which is delivered over a guidewire. The catheter has an angioplasty balloon thereupon. The angioplasty catheter can be deployed over the guidewire, the balloon inflated, the guidewire removed and the tissue illuminated. This procedure is cumbersome and most clinicians prefer not to remove the guidewire once a lesion has been crossed, until the procedure is completed.

SUMMARY OF THE INVENTION

A light diffusing guidewire is described which has a highly flexible distal tip, a torqueable body portion, and presents a low profile to illuminate the luminal wall of very small diameter tubular tissues. The device can be used as a standard guidewire over which a catheter, such as a standard angioplasty-type catheter or an angioplasty-type balloon catheter with an optically clear central channel, can be advanced. Once the balloon and the light diffusing guidewire are deployed at the lesion site, diagnostic and/or therapeutic light can be delivered via the diffusing guidewire through the optically clear balloon catheter to the tissue. Another embodiment can be deployed as a stand-alone device.

It is therefore an object of this invention to provide an intraluminal guidewire for delivering diffuse light to the walls of a tubular tissue wherein the catheter presents a very low profile.

It is a another object of this invention to provide a light diffusing catheter which is steerable.

It is still another object of the invention to provide a light delivery guidewire which may be easily placed in tubular tissues having extremely small lumens and having an outer diameter smaller than the guidewire lumen of conventional guidewire compatible intravascular catheters.

It is a further object of this invention to provide a light delivery guidewire that has a torqueable body portion and a flexible tip.

It is still another object of this invention to provide a light diffusing guidewire which employs a single fiber-optic and may be used to deliver diffuse light to the walls of a tubular tissue.

These and other objects of the invention will soon become apparent as we turn now to a brief description of the drawing and a description of the preferred embodiments.

DESCRIPTION OF THE PREFERRED EMBODIMENT

As stated earlier, in discussing the preferred embodiment of the present invention, it is helpful to discuss the invention in the context of the presently employed intervascular interventional devices and therapies. Such a discussion is meant to be exemplary to teach the essential aspects of the invention in a familiar context and should not be constructed as limiting the light diffusing guidewire of the present invention to intravascular applications. Indeed, applications of the device include the delivery of light to the walls of any ducts and tubular tissues of the body. Such devices include intravascular catheters which deliver light. Such catheters are normally placed in a blood vessel by means of passage over a guidewire. That is, a low profile guidewire which is normally at least in part radio-opaque, is advanced until it reaches or passes the region to be treated. Once the guidewire has been advanced past the region of the vessel to be treated, a treatment catheter is slid over the guidewire and directed thereby to the treatment site. The catheter is then used to deliver the treatment light. Obviously, the catheter must have a larger profile than the guidewire inasmuch as the catheter fits over the guidewire. A "guidewire," as understood in the art of intravascular catheters, refers to a very low profile device which is employed to guide a treatment catheter to a treatment site. In accordance with the present concept of the guidewire, the term "guidewire" as used herein refers to a lumenless elongate member having the dimensions of a guidewire. The term "light diffusing guidewire" refers to a guidewire having the capability of transmitting light along at least a portion of the length thereof and diffusing light therefrom. A light diffusing guidewire in accordance with the above definition has no lumen.

Figure 1:
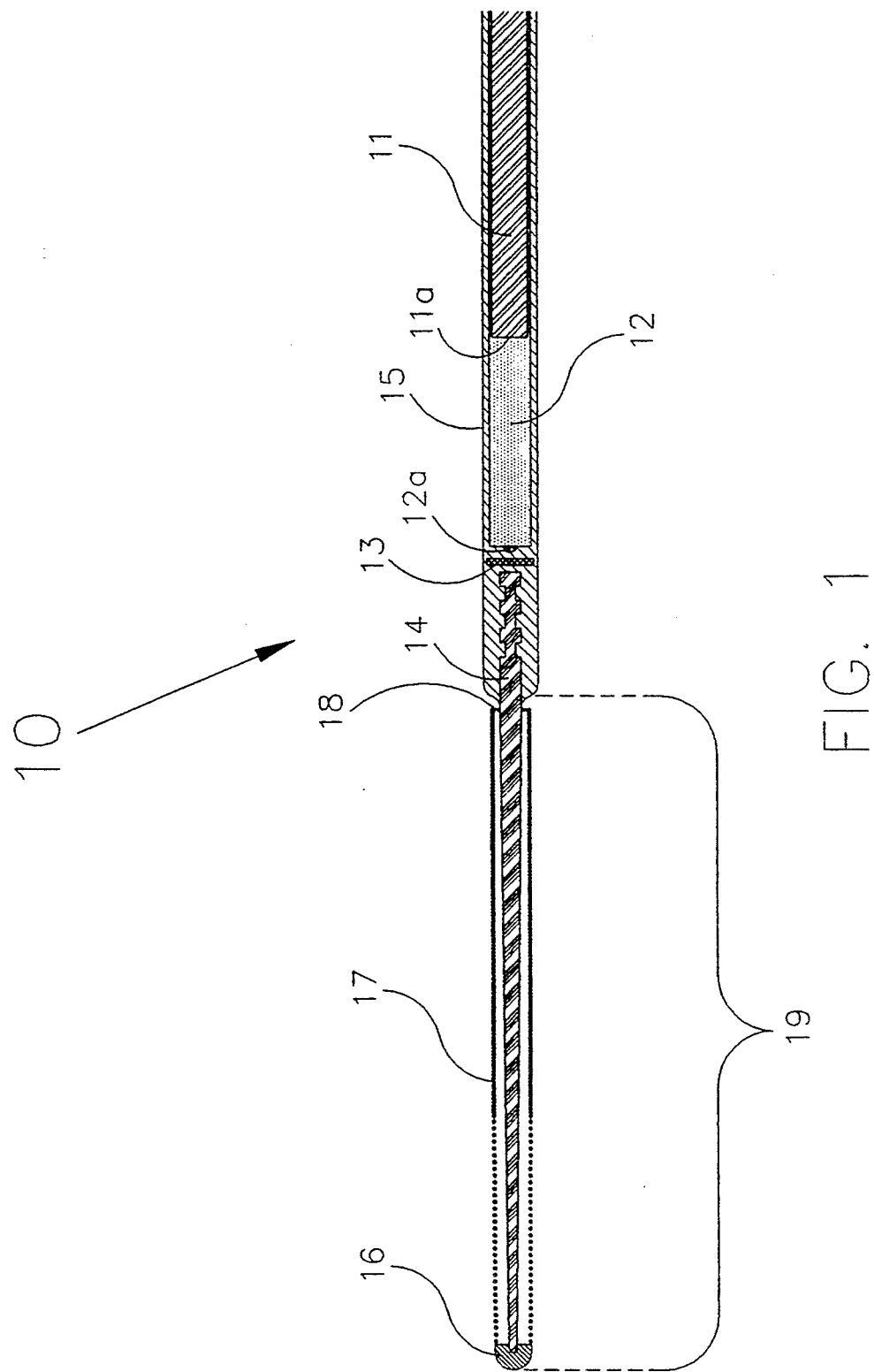
FIG. 1 is a cross-sectional longitudinal view of the distal end of the guidewire according to the present invention.

Referring now to FIG. 1, a light diffusing guidewire in accordance with the present invention is indicated at arrow 10. The single optical fiber 11 with a core diameter from 40–600 micrometers, delivers light from a source (not shown) to a light diffusing element 12. The light diffusing element 12 preferably comprises an optically clear elastomer such as silicone with small (1–25 micron particle size) scattering centers such as alumina particles interspersed therein. The scattering centers can be arranged in such a manner as to produce the desired light output. For example, a continuous non-linear gradient from lowest concentration to highest concentration of alumina in silicone from the optical fiber face 11a to the distal end 12a of the light diffusing element would produce a substantially flat, longitudinally radial light output.

Positioned directly distal to the terminal end 12a of the light diffusing element 12 is a highly reflective disk 13. The highly reflective disk 13 prevents any light which has not been radially distributed from the light diffusing element 12 from advancing distally within the device and impinging upon the central wire 14, potentially causing the heating of the central wire portion 14 of the flexible guidewire tip 19.

Surrounding the optical fiber 11, the diffusing member 12, the reflective disk 13, and the central wire 14, is the external sheath 15. The external sheath 15 can be fabricated from any of a variety of optically clear polymers such as FEP or PFA-Teflon ®. The external sheath 15 positions all said components relative to each other and non-releasably anchors the central wire 14 onto the terminal end of the light transmitting portion of the device 10. The external sheath 15, together with the optical fiber 11 provides the body portion of the guidewire with torqueability. That is, a twisting force applied to the proximal end (not shown) of the body portion will be transmitted to the central wire 14. The central wire 14 consists of a tapered cylindrical wire extending away from the terminal end 12a of the light diffuser element 12 to the distal end of the guidewire 10 where it terminates in the rounded portion 16 of the guidewire tip 19. A coil of wire 17 is attached to a point 18 near the proximal end of the central wire 14 by means of brazing or soldering as is well known in the art. The wire 17 forming the coil is typically a flat, stainless-steel wire with dimensions approximately 0.001" thick by 0.004" wide. The coil of wire 17 terminates in the rounded portion 16 of the guidewire tip 19. As shown, moving to the left from 18 in FIG. 1, the successive turns of wire 17 become spaced further apart as the coil nears the rounded portion 16 of the guidewire tip 19 thereby providing greater tip flexibility. While the tip 19 is extremely flexible, the remainder of the guidewire exhibits reduced flexibility. This enables the guidewire to be torqued during advancement, thereby steering the flexible tip into tortuous lumens.

Figure 2:
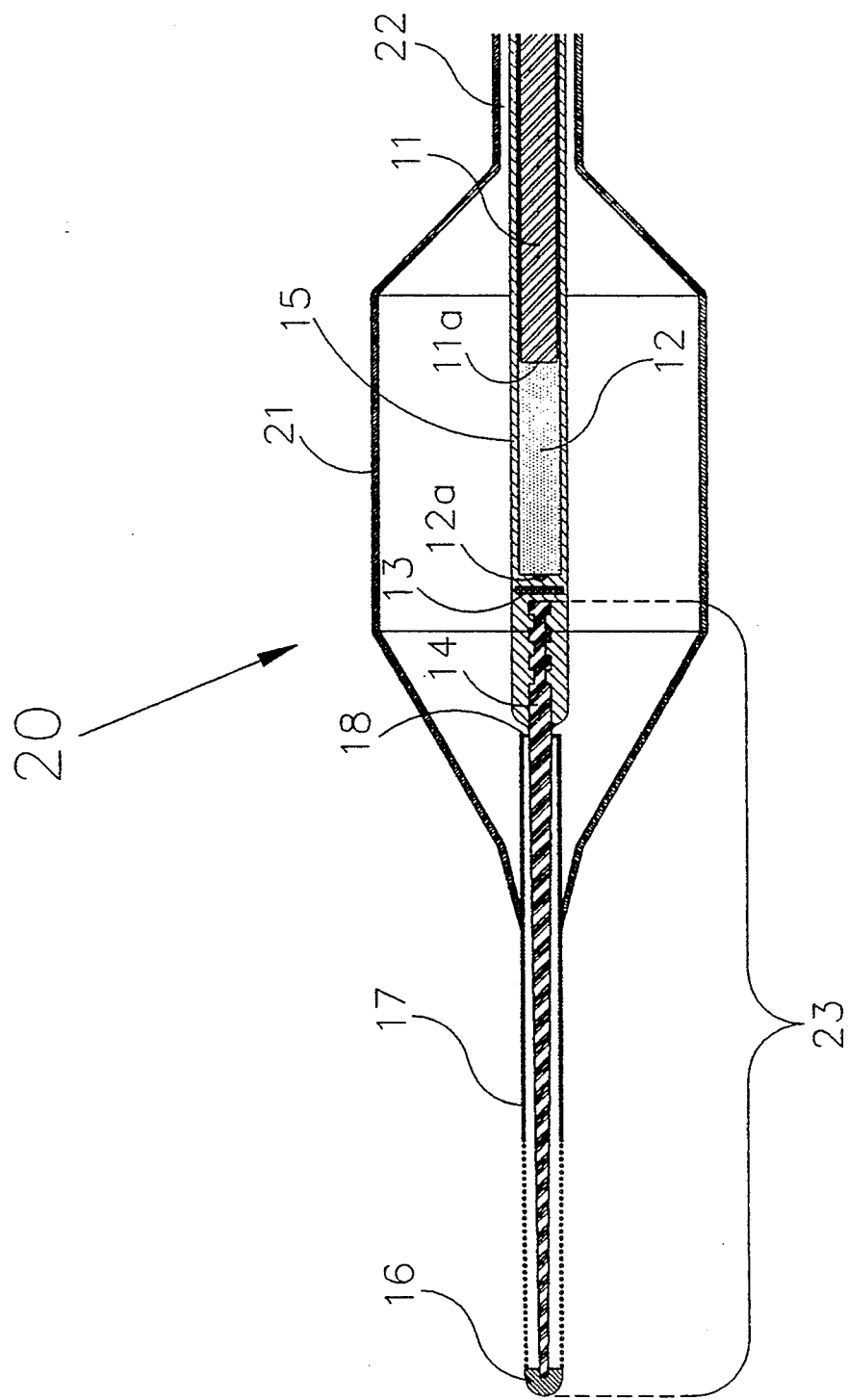
FIG. 2 is a cross-sectional longitudinal view of a balloon integrated with the light diffusing guidewire creating a second preferred embodiment.

FIG. 2 shows a light diffusing guidewire 10 used in conjunction with an inflated balloon 21 with an inflation lumen 22. The balloon is affixed to the guidewire 10 so that the balloon 21 overlies the light diffuser member 12 of the guidewire 10. The wall of the balloon 21 is transparent at the wavelength(s) of light being delivered to (or received from) the surrounding tissue. The light delivery device shown in FIG. 2 provides (a) a transluminal light delivering guidewire having the steerability of a standard guidewire due to its flexible tip 19; and (b) a profile just slightly larger than the cross section of the guidewire itself enabling the introduction into very small tissue lumens; and (c) the ability to displace tissue or fluids surrounding the balloon portion of the guidewire.

Standard guidewire-compatible light delivery catheters have a large profile because they are deployed over a standard guidewire. The fiber optic bundle or single wrapped optical fiber surrounds the guidewire lumen which must be appreciably larger than the outside diameter of the guidewire to facilitate deployment over the guidewire. A light diffusing guidewire according to the present invention can be incorporated into and be integral with a standard interventional light delivery catheter obviating the need for a guidewire lumen and separate light delivery fiber optic bundle and without sacrificing flexibility and providing a greatly reduced profile. For example, the guidewire tip portion, indicated at numeral 23 in FIG. 2, can be affixed to the terminal (invasive) end of any light delivery interventional catheter, thereby eliminating the need for a guidewire. The guidewire tip 23 is conveniently affixed to any such an interventional catheter wherein the light exits the catheter laterally by means of an integral outer sheath 15 as shown in FIGS. 1 and 2.

While particular embodiments of the present invention have been illustrated and described, it would be obvious to those skilled in the art that various other changes and modifications can be made without departing from the spirit and scope of the invention. For example, the light diffusing guidewire, while described for use in a blood vessel, may be also employed in other tubular tissues of the body, such as the urethra, the ureters, the fallopian tubes, esophagus, bronchus, GI tract, bile ducts, tortuous sinus passages or even for the transtympanic illumination of the middle or inner ear. Similarly, the dimensions of the light diffusing guidewire make it possible to employ such a device for delivering light into sinuses having extremely small openings, or even the ears. Such other small lumens are contemplated and are within the scope of the present invention. It is therefore intended to cover in the impending claims all such changes and modifications and applications as are within the scope of this invention.

What I claim is:

1. A light diffusing guidewire comprising a substantially cylindrical elongate member having a proximal end and a distal end and a body portion therebetween and wherein said body portion comprises an optically transparent outer sheath surrounding and enveloping a fiber optic having a proximal end and a distal end, said fiber optic distal end having a light diffusing element affixed thereto and wherein said distal end of said body portion has a guidewire tip extending distally therefrom.

2. The light diffusing guidewire of claim 1 wherein the outer diameter of said body portion is less than 0.038 inches.

3. The light diffusing guidewire of claim 1 wherein said outer sheath surrounds said light diffusing element and at least a portion of said guidewire tip.

4. The light diffusing guidewire of claim 1 further comprising an inflatable member affixed to said outer sheath wherein said inflatable member overlies said light diffusing element.

5. A light diffusing guidewire comprising an elongate member having a proximal end and a distal end and a body portion therebetween and wherein said body portion consists of a transparent outer sheath surrounding a fiber optic having a distal end with a cylindrical light diffusing element affixed thereto and wherein said distal end of said body portion has a guidewire tip extending distally therefrom and wherein said guidewire tip further comprises a tapered wire with a second wire coiled therearound.

6. The light diffusing guidewire of claim 5 wherein said outer sheath surrounds said cylindrical light diffusing element and at least a portion of said guidewire tip.

7. The light diffusing guidewire of claim 5 further comprising an inflatable member affixed to said outer sheath wherein said inflatable member overlies said light diffusing element.

8. A method for delivering light to a target on or near the wall of a lumen comprising the steps of:
    (a) inserting the distal end of a light diffusing guidewire in accordance with claim 1 into the lumen;
    (b) advancing the distal end of the light diffusing guidewire through the lumen until the diffuser element is adjacent to the target;
    (c) introducing light into the guidewire to illuminate the target.

9. The method of claim 8 wherein the light diffusing guidewire has a balloon element overlying the light diffuser element and comprises the additional steps of inflating the balloon before performing step (c) of claim 8 and deflating the balloon after step (c) of claim 8 has been performed.

10. The light diffusing guidewire of claim 1 further comprising a light reflecting element disposed between said light diffusing element and said guidewire tip.

11. The light diffusing guidewire of claim 5 further comprising a light reflecting element disposed between said light diffusing element and said guidewire tip.

* * * * *